US012270805B2

(12) United States Patent
Fauvet et al.

(10) Patent No.: US 12,270,805 B2
(45) Date of Patent: Apr. 8, 2025

(54) ISOTOPIC MARKING AND IDENTIFICATION OF ANIMALS AND PLANTS

(71) Applicant: IDS GROUP, Meyzieu (FR)

(72) Inventors: Patrice Fauvet, Lyons (FR); Valérie Migeon, Lyons (FR)

(73) Assignee: IDS GROUP, Meyzieu (FR)

( * ) Notice: Subject to any disclaimer, the term of this patent is extended or adjusted under 35 U.S.C. 154(b) by 0 days.

(21) Appl. No.: 18/086,299

(22) Filed: Dec. 21, 2022

(65) Prior Publication Data

US 2023/0126230 A1   Apr. 27, 2023

Related U.S. Application Data

(62) Division of application No. 16/626,208, filed as application No. PCT/EP2018/066959 on Jun. 25, 2018, now Pat. No. 11,561,214.

(30) Foreign Application Priority Data

Jun. 26, 2017 (FR) ...................... 1755826

(51) Int. Cl.
*G01N 33/24* (2006.01)
*A01K 11/00* (2006.01)
*G01N 33/02* (2006.01)
*G01N 33/483* (2006.01)

(52) U.S. Cl.
CPC ............. *G01N 33/24* (2013.01); *A01K 11/00* (2013.01); *G01N 33/02* (2013.01); *G01N 33/483* (2013.01); *G01N 33/245* (2024.05)

(58) Field of Classification Search
CPC ........... G01N 33/483; G01N 2033/245; G01N 33/24; G01N 33/02; G01N 1/14; G01N 27/02; G05D 11/00; G05D 11/138; A01C 17/006; A01C 21/007; A01C 21/00; G05B 15/02; A01K 11/00
USPC .................. 700/266, 284; 702/22, 23, 30–31
See application file for complete search history.

(56) References Cited

U.S. PATENT DOCUMENTS

| 5,668,719 | A  | * | 9/1997 | Bobrov ............... A01C 21/007 |
| | | | | 702/2 |
| 5,887,491 | A  | * | 3/1999 | Monson ................. G01N 33/24 |
| | | | | 73/864.74 |
| 9,107,341 | B2 | * | 8/2015 | Martinez ............. G05D 11/138 |
| 10,620,180 | B2 | * | 4/2020 | Martinez ............. G05D 11/138 |
| 10,663,447 | B2 | * | 5/2020 | Martinez ............... G05B 15/02 |
| 11,085,909 | B1 | * | 8/2021 | Berg ..................... G01N 33/24 |
| 2006/0178847 | A1 | * | 8/2006 | Glancy ................. A01G 20/00 |
| | | | | 702/62 |

(Continued)

*Primary Examiner* — Shogo Sasaki
(74) *Attorney, Agent, or Firm* — B. Aaron Schulman, Esq.; Stites & Harbison, PLLC

(57) ABSTRACT

An isotopic identification method is provide that makes it possible, where appropriate, to link a livestock animal or animal product to a specific farm, or a plant or a plant product to a farm, by analyzing the concentration of ratios or stable isotopes, and comparing with isotopic codes previously generated in a unique fashion for a set of frames. A method is also provided that makes it possible to impose a unique code on the animals of a farm or on the plants of a farm, and a computer making it possible to store the unique codes generated in memory is provided to generate unique codes for new farms and to perform comparisons.

20 Claims, 5 Drawing Sheets

(56) References Cited

U.S. PATENT DOCUMENTS

| | | | | |
|---|---|---|---|---|
| 2006/0254138 A1* | 11/2006 | Bissonnette | ............ | A01G 31/00 47/60 |
| 2006/0254371 A1* | 11/2006 | Shiloni | .................... | E02D 1/06 73/864.34 |
| 2010/0332039 A1* | 12/2010 | Danieli | .................. | A01G 25/16 700/284 |
| 2013/0226347 A1* | 8/2013 | Martinez | .............. | A01C 21/007 700/266 |
| 2015/0301011 A1* | 10/2015 | Martinez | .............. | A01C 21/007 702/2 |
| 2015/0301536 A1* | 10/2015 | Martinez | ................ | G01N 33/24 700/266 |
| 2020/0240971 A1* | 7/2020 | Martinez | ................ | G01N 33/24 |

\* cited by examiner

ISOTOPIC MARKING AND IDENTIFICATION OF ANIMALS AND PLANTS

CROSS-REFERENCE TO RELATED APPLICATIONS

This application is a Divisional Application of U.S. application Ser. No. 16/626,208, having a filing date of Dec. 23, 2019, which was a National Stage application of International application PCT/EP2018/066959, filed Jun. 25, 2018, which claims priority to French patent application FR 1755826, filed Jun. 26, 2017, all of said applications being incorporated herein by reference.

FIELD OF THE INVENTION

The present invention relates to the marking of animals and plants. It in particular relates to a method for isotopic identification of an animal or a plant and its byproducts, as well as a method making it possible to impose a unique code on this animal or plant, and its byproducts. The invention lastly relates to an information recording medium and an electronic computer for carrying out such a method.

BACKGROUND OF THE INVENTION

The possibility of determining the origin of animal or plant materials in agri-food products has become a major food safety issue and a market penetration factor for farmers and processors in the sector. Large-scale distribution is also increasingly concerned due to its involvement or near-integration in the sector by purchasing whole production lots or intervening directly with farmers.

SUMMARY OF THE INVENTION

The present invention aims to propose a method making it possible to impose, safely and reproducibly, a unique code on an animal or a plant and its byproducts, making it possible to determine its origin, preferably with a precision reaching as far as its farming or growing location.

It in particular aims to provide an assigned unique code allowing traceability at different granularity levels, for example the farm, or much finer, such as species or varieties, production type, and optionally, the date of the production lot or cycle.

Another aim of the invention is to propose a safe and reproducible method for identifying an animal or a plant and its byproducts, making it possible to determine its origin, preferably with a precision reaching as far as its farming or growing location.

Still another aim of the invention is to provide such methods suitable for managing several or many farming or growing locations, and preferably without limitation regarding the number of farming and growing locations.

Another aim is to provide such methods that are economically viable.

DETAILED DESCRIPTION OF EXEMPLARY EMBODIMENTS

These aims as well as others are in particular achieved owing to the use of a predefined model (M) used to impose, on the animals or plants, a unique isotopic code specific to a farm or farm subset, respectively farm or field, and optionally even finer granularity levels (e.g., species or varieties, production type, optionally lot), this code being based on the nature, the concentrations or the ratios of stable isotopes of chemical elements. These aims as well as others are also achieved by measuring and knowing concentrations of isotopes of major elements contributed by the diet and found in an extent able to be anticipated and analyzed in the animals and plants, and making it possible to contribute signature elements regarding the production cycles, for example. Over the course of the deployment of the solution on several farms, unique codes can be generated for each of them, taking account of the codes previously generated for other farms. All of these codes can be recorded in the model (M), preferably housed in an electronic computer or the like. Each unique code corresponds to the isotopic signature of the animal or the plant at the time of slaughter or harvest, respectively. This code no longer varies after slaughter or harvest, and therefore also marks the products coming from the animals and plants thus marked. The effect of metabolism, absorption, accumulation or elimination of the markers is stopped upon slaughter or harvest. The invention accounts for the important points that are the moment of the marking cycle (that is to say, the diet with isotopic food) and its duration. This code is the result of an isotopic food determined by the model (M) and applied by the farmer or the grower according to the instructions given by the model. To arrive at this unique code upon slaughter or harvest, the model (M) accounts for the accumulation rate (TA) of the elements and/or isotopes in the animal or plant as a function of the feeding or watering diet with this isotopic food. Feeding diet in particular refers to the feeding duration of the animals or watering duration of the plants with the isotopic food, and the feeding period(s) with this isotopic food. It can for example be contributed over a single period or several periods, for example 2 or 3. It can be done just before the slaughter or harvest, or further upstream. As an example in chickens, in order to ensure the presence of the markers at the time of slaughter or harvest, it is in particular possible to contribute the isotopic food from the $11^{th}$ day to the $33^{rd}$ day, or from the $24^{th}$ day to the $33/34^{th}$ day before slaughter. This code can also incorporate the so-called major markers, which have a variability depending on the cycles and in particular the composition of the food. The parameters can have been determined beforehand through tests on a population of this animal farm or subset, or this farm or field. Preferably and advantageously, the choice of the elements and their isotopes, and their respective ratios that the Model (M) determines for each animal farm or subset, or for each farm or field, is based on the prior knowledge of what is called here the basal geochemical signature (BGS) of the animal farm or subset, or of the farm or field. This BGS, as will be described hereinafter, is the knowledge of chemical elements, their stable isotopes, their respective concentrations or ratios, within the farm or its subset, or the farm or field, prior to the imposition of the code by an isotopic food. The model (M) can advantageously incorporate the ability to define an isotopic food making it possible to impose said unique code, by varying the stable isotopes of elements present in the BGS as well as their concentrations or ratios. Preferably, the model (M) will do this in the most minimalistic way possible and while taking account of the price, production mode of the isotopes/enrichment level/strategy of the isotopes as a function of the markets, and/or the availability of the isotopes so that the price of the isotopic food is as low as possible. All of these features apply to the objects of the invention defined in more detail below. This model (M) can further make it possible, if applicable, to couple a farmed animal or an animal product with a determined farm or farm subset, or a plant or plant product with a determined animal farm or field, by analyzing concentrations or ratios of stable isotopes, making it possible to determine a concentration or ratio profile of these stable isotopes, in particular by mass spectrometry, and to compare with the unique codes recorded in the model (M). Certain elements and their isotopic distribution (ratios of stable isotopes C, H, O, N, S) vary over course of the year, for example as a function of food or water contributions. The invention also makes it possible to determine the production cycle of the animal or plant, from a sample thereof.

Within the meaning of the invention, a byproduct in particular refers to anything derived from the animal or plant. This may in particular be a raw piece (for example including flesh and/or bone and/or skin, for example, half-chicken, turkey or chicken thigh, etc.), cut and isolated parts (for example flesh, organs, skin, bones, nails, fur, feathers, egg shells, flower, stem, etc.), products derived from the animal or plant (for example eggs, fruits, seeds, etc.). The method according to the invention can be applied to an animal for slaughter, but is not limited thereto. Indeed, it can also be used to track animals that are not intended for slaughter, such as sport or work animals (horses, donkeys, mules, dromedaries, camels, etc.) or pets (dogs, cats). The method can also be used to track plants of value, for example old trees or plants derived from noble selections, such as rosebushes, orchids, etc.

The invention thus in particular relates to an isotopic identification method and a method making it possible to impose a unique code, such as an electronic computer.

Isotopic Identification Method

The isotopic identification method making it possible, if applicable, to couple a farmed animal or an animal product with a determined farm or farm subset, or a plant or plant product with a determined farm or field, by analyzing concentrations or ratios of stable isotopes, may in particular comprise:

a—in a sample derived from the animal/plant or the product of an animal/plant to be identified, measuring concentrations (C2) or ratios (R2) of stable isotopes, then obtaining a profile of concentrations or ratios of these stable isotopes, in particular by mass spectrometry, b—comparing this profile with profiles recorded in a predefined model (M) containing, in memory, profiles in the form of unique codes each suitable for an animal farm or farm subset or a farm or field, each unique code having previously been generated by the model (M) and applied uniquely to the animals of a farm or farm subset or to the plants of a farm or field by an isotopic food delivered to these animals/plants such that, at the time of their slaughter/harvest, the concentrations or ratios of these stable isotopes in these animals/plants are substantially identical to the unique code, c—concluding that the animal/plant or the product from an animal/plant to be identified has a profile substantially equal to a recorded code (possible use of an interval with a minimum value and maximum value) and further indication of the animal farm or farm subset/farm or field of origin, if, at the end of the comparison, the profile corresponds to a recorded profile and otherwise, concluding that the animal/plant or the product does not come from any animal farm or farm subset/farm or field whose code is recorded in the model.

Hereinafter, the term "farm subset" will not always be used at the same time as farm, but it will be considered to be comprised in the term "farm".

Hereinafter, the measurements of concentrations (C2) or ratios (R2) of stable isotopes of several elements make it possible to obtain isotopic profiles in isotope ratios of a same element, and also preferably ratios between chemical elements. The measurements are done using reliable measuring methods for the considered elements (see later).

Preferably, in step a—, the concentration or the ratios are measured of one or several, preferably all, of the stable isotopes of the following chemical elements:

at least 5, 10, 15, 20, 25, 30, 35, preferably all of the following elements: Li, Be, B, F, Na, Mg, Al, P, Cl, K, Ca, Ti, V, Cr, Mn, Fe, Co, Ni, Cu, Zn, Ga, Ge, As, Se, Rb, Sr, Y, Zr, Nb, Mo, Rh, Pd, Ag, Cd, Sn, Sb, Te, I, Ba, Hf, Ta, W, Re, Ir, Hg, Ti, Pb, Si, at least 5, 8, 12, preferably all of the following elements: La, Ce, Pr, Nd, Pm, Sm, Eu, Gd, Tb, Dy, Ho, Er, Tm, Yb, Lu and/or, preferably and, C, O, N, H, S (preferably all, but not excluding 2, 3 or 4 of them).

Preferably, the predefined model (M) comprises the unique codes of animal farms or of farms or fields, defined by the concentration or the ratios of one or several, preferably all, of the stable isotopes of the following chemical elements such that they can be measured at the time of the slaughter/harvest in the animals from these farms/plants from these farms or fields:

at least 5, 10, 15, 20, 25, 30, 35, preferably all of the following elements: Li, Be, B, F, Na, Mg, Al, P, Cl, K, Ca, Ti, V, Cr, Mn, Fe, Co, Ni, Cu, Zn, Ga, Ge, As, Se, Rb, Sr, Y, Zr, Nb, Mo, Rh, Pd, Ag, Cd, Sn, Sb, Te, I, Ba, Hf, Ta, W, Re, Ir, Hg, Ti, Pb, Si, at least 5, 8, 12, preferably all of the following elements: La, Ce, Pr, Nd, Pm, Sm, Eu, Gd, Tb, Dy, Ho, Er, Tm, Yb, Lu and/or, preferably and, C, O, N, H, S (preferably all, but not excluding 2, 3 or 4 of them).

Later, we will see preferred management modes of the elements and their ratios, combining measurements of some of them, preferably at each farming or growing cycle, and variations of some of the others by the feeding and or feed, watering or spray water.

Preferably, this unique code for a farm or field has been determined by the predefined model (M), and imposed on the animals from the farm or the plants from the farm or field by the isotopic food distributed such that this code is integrated by the animal when it is slaughtered or the plant when it is harvested. In this way, all of the farms or fields produce animals/plants having this unique code and the model M has, in memory, all of the unique codes generated at a given time. It will be seen later that the imposed variations of certain isotopes are also regulated by the feeding or water supply regimen, preferably over a continuous or divided sub-period of a period or a farming or growing cycle, designed to result in the unique code at the time of the slaughter or harvest.

Preferably, step a—comprises, for each chemical element, the determination of the variations of one or several minor stable isotopes relative to the most abundant one.

Preferably, the concentrations or ratios of isotopes are measured by mass spectrometry (MS). It is in particular possible to use inductively-coupled plasma mass spectrometry, or ICP-MS, multi-collector plasma source mass spectrometry, or isotope ratio mass spectrometry, or IRMS, or any other technique making it possible to identify and measure the elements and their stable isotopes, with their concentrations or their ratios, for example expressed in ratios of the minor stable isotope(s) relative to the most abundant stable isotope in the sample. It is thus also possible to conduct concentration analyses by laser ablation inductively-coupled plasma mass spectrometry (LA-ICP/MS) or by laser-induced breakdown spectroscopy (LIBS).

The method can in particular comprise the use of a programmable electronic computer, provided with a programmable logic unit, an information recording medium and a data exchange interface connected between them by an internal data bus. The electronic computer can also include a man-machine interface.

The method can therefore comprise the acquisition, by the electronic computer, of concentration (C2) or ratio (R2) values, in particular as measured by MS, forming the isotopic signature of an animal, a plant or a product from this animal or this plant, for which one wishes to know whether it comes from a farm, a subset of a farm, or a farm or field whose unique code is known or recorded in the electronic computer, and if applicable, to determine the exact origin.

The computer can therefore also make the comparison between the data acquired by the computer and the recorded unique codes that it has a memory. The computer can next determine, through this comparison, whether the acquired profile corresponds to a recorded unique code, and in the first case deliver the identity of the animal farm or farm subset, or the farm or field, or then conclude that there is no match. Regarding the acceptable degree of variability, each newly created unique code is defined in a value interval, or the computer contains instructions to apply a certain level of variability, for each isotopic element, which in particular accounts for the metabolization or the accumulation of markers by a species or a variety. Hence the presence in the computer of data related to the species. In general, it can be considered that the metabolization or accumulation of markers is about 15-20% via ingestion by the water (liquid) and about 30 to 40% via animal feed (solid food). The quantities of isotopes ingested daily may for example be, in particular for poultry, between 1 per 1000 and 50 per mil, e.g., 30 per mil with respect to the target values ultimately measured. More specific data can be generated and recorded in the computer, these data being able to result from experimentation, in particular experimentation on the farming or growing site. The term "substantially" used here accounts for this variability, the method according to the invention simply allowing a variability that does not challenge the generation of a unique code (with the isotope by isotope variations), or the ability to effectively compare a signature measured in a sample and a unique code. The determination of a code for a farm or a crop accounts for these variabilities to define a reliable unique code. "Substantially" can in particular signify a deviation of at most 5, 4, 3, 2, 1, 0.5 or 0.1% for the concentration or the ratio.

The invention makes it possible to identify the origin of the products coming from animals and plants, inasmuch as these animals and plants belong to the farm and crop management program of the present invention. Regarding animals, it is possible to benefit from this traceability on whole animals as well as parts of animals, for example flesh, bone, skin, organs, etc., as was explained supra.

As will be seen later, the computer is also programmed to make it possible to identify the farming cycle or the slaughter date, or the growing cycle or the harvest date. In this case, the measurement of the majors and their isotopes (C, H, O, N, S, preferably all of them) in the food and/or the water upon each cycle, which vary from cycle to cycle due to variations in the foods and in the water, are recorded cycle after cycle in the recording medium of the computer, and the computer is programmed to be able to compare the values of these majors in a sample of the animal or the plant, and to make the connection with the values of majors between different cycles recorded in the recording medium.

Method Making it Possible to Impose a Unique Code

The method making it possible to impose a unique code specific to the animals of a farm or a subset of a farm, or to the plants of a farm or a field, including the products, in particular food products, from these animals or plants, this method being suitable for implementing the aforementioned isotopic identification method, can in particular comprise:

i—analyzing the abundance of stable isotopes of several elements (a) in the water of the farm and/or in the food given to the farm and/or the soil and/or in organic samples of the animals from the farm (dark or white meat, organ, skin and/or bone) of animals from the farm of at least one farming cycle, or (b) in the spray water for the crop and/or the soil and/or in the plant from at least one growing cycle, one thus obtains the basal geochemical signature (BGS) of the farm or the farm subset, or of the farm or the field, 2i—selecting several elements having stable isotopes among those present in the BSG, one provides the animals or plants from this cycle or future farming or growing cycles, with an isotopic food comprising a determined abundance (e.g., ratios of the isotopes of a same element) of stable isotopes of the selected elements, this abundance being calculated while taking account of the accumulation rate (TA) of these animals or plants, owing to which, at the moment of the slaughter of the animal or harvest of the plant and in light of the BSG of the farm or the crop, a unique code is imparted to the animals or plants from this farm, respectively crop.

In one embodiment, it is possible to enrich with one or several isotopes, or deplete with one or several isotopes, or combine enrichment and depletion, with respect to what an unmodified diet would contribute to the animals or plants during a given cycle.

It will be seen later that it is possible to measure the isotope ratios in a larger or smaller number of elements, in particular among the elements allowing a finer geographical discrimination. The larger this number is, the more the basal signature BGS already represents a high degree of precision regarding the farm, since it is possible to reduce the number of elements for which a modification of the isotope ratio will be imposed. This is why it will be said that there is initially preferably a variation of at least 3 elements, but one skilled in the art now understands perfectly that it is possible to modify, in particular to increase this number to have enough precision.

Preferably, in step i, the abundance of stable isotopes of several elements is analyzed in the flesh, skin, and/or bones of animals from the farm, or in the tissues of plants (stem, leaf and/or seeds), and the BGS or an element of the BGS from the farm or crop is thus obtained.

Preferably, in step i, the abundance of stable isotopes of several elements is analyzed in the water and food used for consumption by the animals, and one thus obtains the BGS or an element of the BGS of the farm or the farm subset.

The isotope concentration in the animals and plants is also related to the farming or growing site, through the contributions to the soil and the available water. Preferably, in order to define the BGS, the isotope concentration or ratios of the food and water are analyzed upon each farming and growing cycle. Preferably, in order to define the BGS, control analyses are done on the animals or plants, in order to verify the presence of the isotopes that one has chosen to vary, as well as their concentration or ratios.

Preferably, all of these measures are taken in order to define the BGS.

The BGS can substantially correspond to the isotopic signature that an animal or plant of the farm would have, fed in the conventional manner on the farm, therefore without intervention by isotopic food or imposed isotopic variations.

The animals may have noncontrolled or non-isotopic food, and likewise the plants can receive noncontrolled or non-isotopic water. One or several of the regular analyses (for example, 1 per cycle, in concentration) of the soil or water in particular can be done. The model (via the computer) can account for the observed variations, it can deem them insignificant to obtain the unique code, or it can decide to make a correction, for example to modify the code.

Preferably, in the step 2i, a period is defined during which the animals receive the isotopic food, so as to obtain, at the time of slaughter, animals having acquired the unique code specific to the farm or the farm subset. This period is advantageously a fraction of the farming or growing cycle. This period is sufficient for the unique code to be present at the time of the slaughter or harvest. If one wishes to provide figures, in terms of time, said period preferably represents less than ⅓, ¼, ⅕ or ⅙ of the farming or growing cycle.

This unique code is a set of concentrations or ratios of stable isotopes of a certain number, sufficient and representative, of the elements cited above in 3 lists.

Preferably, certain elements and their isotopic distribution are associated with cycle location and/or identification functions. Thus, certain elements and their isotopic variations are connected to a rough geographical location (e.g., regional), others to a fine location (e.g., farm, parcels, etc.), others to a farming or growing cycle (in particular knowing isotopic ratios of food or water contributions). Lastly, some of the elements and their isotopic ratios are markers on which the variation is imposed for finalization of the unique code.

The natural isotope makes it possible to perform a regional geolocation. It is generally based on analyses of what are called the 5 majors (C, H, O, N, S) and the interpretation of the isotopic ratios done from an appropriate analytical instrument, preferably of the IRMS type. The concentrations or the ratios of the isotopes of these majors are preferably measured, for all 5, or that at least 2, 3 or 4 of them. In one embodiment, a regional geolocation is therefore done from these majors, under the conditions just described.

In order to provide an even more precise geographical origin and collaborate in obtaining a signature including a finer geographical origin, in one preferred embodiment, in particular in addition to the previous one, measurements are used of isotope ratios of elements capable of signing a geographical origin finer than the majors. These elements are those of the other two lists mentioned supra. Among these lists, there are certain elements, such as Sr, B, Li, Ca, Na, Mg, K, F, P, Cl, As, Pb, Cd, that make it possible to discriminate between nearby, or even adjacent, geographical locations. Preferably, these elements are measured (all of them or a representative and discriminating number, in particular at least 5, 6, 7, 8, 9, 10, 11, 12 or all), in isotope concentration and preferably ratio. Sr, B and Li are geographical trace elements, markers of the soil and water, and are found in the animal or plant in specific concentrations and ratios. Preferably, the concentrations or ratios of these 3 elements are also measured. Ca, Na, Mg, K, F, P and Cl are major trace elements contributed by the food and water. Preferably, one chooses not to vary their concentrations or ratios so as to keep their ability to give or mark a fine geographical location, such as Sr, B or Li, or in combination with the latter. The possibility is therefore also provided of measuring their isotope concentrations or ratios. The elements As, Pb and Cd can also be used in the same way, by determining their concentration or the ratios of their stable isotopes. It is therefore possible to combine at least two or all three groups of elements.

However, in order to truly distinguish between farms or crops in a same location, or even adjacent parcels, a unique signature means (called imposed) is added via traces (stable isotopes) whose natural abundance will be varied/doped. To do this, the ratios of certain isotopes are varied, preferably elements other than those of the preceding paragraph, that will in particular be chosen from the lists mentioned supra. These isotopes are in particular chosen from among Be, Al, Ti, V, Cr, Mn, Fe, Co, Ni, Cu, Zn, Ga, Ge, Se, Rb, Y, Zr, Nb, Mo, Rh, Pd, Ag, Sn, Sb, Te, I, Ba, Hf, Ta, W, Re, Ir, Hg, Ti, Si; optionally also from among La, Ce, Pr, Nd, Pm, Sm, Eu, Gd, Tb, Dy, Ho, Er, Tm, Yb, Lu. Advantageously, it is chosen to vary the ratios of isotopes whose elements are naturally present in animals or plants from the farm. It is chosen to vary the ratios of isotopes for a sufficient number of elements for the discrimination, and it is in particular possible to set a minimum of 3, 4, 5, 6, 7, 8, 9 or 10 elements.

The majors (C, H, O, N and S) can also be production markers, in that their isotopic ratios vary with the food and water, as a function of the time of year and variations in composition of the food and water during the year. In one embodiment, the ratios in the food and water are measured or known for each farming or growing cycle, as well as their impact on the isotopic signature of the animal at the time of slaughter or the plant at the time of harvest. This element of the signature contributed by C, H, O, N and S (or a discriminant subset of 2, 3 or 4) then makes it possible, upon analysis of the animal, plant or byproducts, to go back (in addition to the geographical origin or the farm) to the farming or growing cycle, and more specifically the date of slaughter or harvest.

Preferably, the method comprises, during a farming or growing cycle, at least one analysis of the isotopic supply, namely of the water and/or food, in order to detect a potential variation in the abundance of the stable isotopes of the selected elements.

Preferably, the method comprises using an electronic computer in which the unique codes are stored specific to the other farms or farm subsets, or to the other forms or fields, previously determined and recorded.

The programmable electronic computer is preferably provided with a programmable logic unit, an information recording medium and a data exchange interface connected between them by an internal data bus. The electronic computer can also include a man-machine interface.

Preferably, the data measured in order to establish the BSG of the farm or farm subset, or of the farm or field in question are entered in the computer, the latter, through its programmable logic unit, being able to determine the BSG or geochemical passport, which establishes the reference starting base for a given site.

Preferably, the computer stores the data of the TA of the animals of the farm or subset, or plants, in particular as a function of the farming, respectively growing conditions, and preferably has computing means making it possible to establish a correlation between a variation in abundance of isotope elements and the feeding diet with the isotopic food, in order to obtain a unique code of the time of slaughter, respectively harvest. The TA is dependent on the quantity of food (solid and/or liquid) absorbed by the animals or plants during their life or growth cycle and the metabolization or absorption rate, which the computer can take into account for the normal food and the isotropic food.

Preferably, the computer stores the BGS of the farm or its subset or of the farm or field. It also stores the unique codes specific to other farms or farm subsets, or other farms or fields, that have been established during an earlier period. The computer can compute and propose to the user, an abundance variation of the isotopes in order to define the isotropic food and the diet with this isotropic food (that is to say, duration and schedule relative to the slaughter or harvest date) in order to give the animals from the farm or farm subset the unique code specific to the moment of the slaughter, respectively to give the plants the unique code specific to the moment of the harvest.

According to one advantageous feature, the computer incorporates the geochemical passport assigned to each farm, and in particular contains all of the geochemical passports of the farms on which the model has been deployed. Each passport is stored in the database and can be modified for updates or to add additional information. This passport is in particular made up of the BGS, and can comprise additional elements, the designation of the species, the subspecies, the variety, isotropic variations during the various farming or growing cycles, variations for example related to the season, in particular with the isotropic variations in the feed or watering water, rainfall patterns, whether the "organic" qualification applies, farming or growing practices, generally all of the elements referring to a given site. All of these data can be viewed and some of them can be integrated as variables into the definition of a diet and an isotopic food in order to impart the unique code at the time of the slaughter or harvest, despite seasonal variations or other variable elements.

We have seen that the computer operates during the characterization phase. It determines the variations in isotopic abundance required to introduce the unique code for the targeted site/farm. If a significant change is observed related to the analysis of the water or animal food or soil in terms of concentration, the computer may also be used to recalculate the variations in abundance of the required isotopes, in order to obtain a unique code. However, these variations are minimal, and a deviation between 1 per 1000 and 3 per 1000 may be done.

Preferably, the computer knows (the user having recorded these data) and takes account of one or several, preferably all, of the following variables:
the animal species or plant variety,
the farming duration before slaughter or the growing duration before harvest,
optionally the feeding duration and the theoretical feeding calendar with an isotopic food,
the accumulation rate TA of the animals or plants under the farming, respectively growing conditions.
any uncontrolled contribution of food (for example in open-air farming, rain for plants),
data relative to the soil (in particular on organic farms).

Once the site characterization phase is complete and recorded in the computer, it is advantageously possible, before defining the isotopic feed and its administration regimen, to perform a control analysis on the animals or the plants, in order to verify that what the geochemical passport contains as stable isotopes and their concentrations/ratios is still valid. One may settle for analyzing the muscles (white and dark) for the animals.

Preferably, the unique code integrates an isotopic signature of several rare elements, in particular at least 5, 8, 12, preferably all of the following elements: La, Ce, Pr, Nd, Pm, Sm, Eu, Dg, Tb, Dy, Ho, Er, Tm, Yb, Lu. It can be specified that these rare elements are primarily associated with the geographical location of the farm or of the farm or field, in particular at the continent, country or region level.

Preferably, the unique code integrates an isotopic signature of one or several elements, in particular at least 5, 10, 15, 20, 25, 30, 35, preferably all of the elements Li, Be, B, F, Na, Mg, Al, P, Cl, K, Ca, Ti, V, Cr, Mn, Fe, Co, Ni, Cu, Zn, Ga, Ge, As, Se, Rb, Sr, Y, Zr, Nb, Mo, Rh, Pd, Ag, Cd, Sn, Sb, Te, I, Ba, Hf, Ta, W, Re, Ir, Hg, Ti, Pb, Si. This signature element is in particular related to the identity of the farm or its subset, or of the farm or field, and optionally of the animal or plant species.

Preferably, the unique code integrates an isotropic signature of the elements C, O, N, H, S, which is in particular related to the food (solid and/or liquid).

Preferably, the unique code comprises these three isotropic signatures.

In one preferred embodiment, the unique code comprises stable isotope concentrations or ratios of major elements, namely C, O, H, N and/or S, obtained after measuring concentrations (C3) or ratios (R3) of these isotopes in the food and correction by the rate of accumulation in the animal or plant in question. The elements (C, H, O, N and S) are the so-called major elements. Their level can in particular vary from one cycle to another in a year, and this variation can be known (the concentrations are measured in the food lots or in the water) and taken into account in the unique code, allowing traceability at different granularity levels, for example the farm, or much finer, such as species or varieties, production type, and even lot (production cycle).

The computer can also comprise the data relative to the concentrations (C3) or ratios (R3) of the major isotopes (C, H, O, N and S) in the food, and their translation into concentrations or ratios that will be found in the animals or plants at the time of the slaughter, respectively harvest, depending on the metabolization or the rate of accumulation. The computer is able to compute the corrected values foreseeable by correction by the rate of accumulation in the animal or plant in question.

The electronic computer can also be configured with environmental data, species, marking cycle data (short, long, multi-stage), geographical data, or reference nutritional elements. All of these data make it possible to generate a unique code adapted to the target location. It must also be specified that the computer can advantageously be configured with the known reference nutritional values, the toxicity values, and any other criteria, which will allow it to define unique codes (and therefore isotopic recipes and diets) while avoiding generating invalid codes that deviate from these criteria.

The computer computes and proposes the stable isotope abundance variations and/or the isotopic food regimen to impart the unique code at the time of the slaughter or harvest. Preferably, the computer is programmed to determine these abundance variations in an optimized manner in terms of price and/or availability of the isotopes. The user can thus record data relative to these abundance variation, price and availability variables, and keep them up to date over time, so that the computer best manages the definition of the elements and isotopes to be varied, therefore to add into the food in order to produce the isotopic food. The criterion that the computer always respects is to define the elements and their isotopes, and their concentrations or ratios, in order to define a new unique code, different from those already established for other farms or subsets, or farms or fields.

Preferably, in order to adjust the isotope ratios of the isotopic food, the abundance of stable isotopes is varied (or the computer proposes to vary it) of the following chemical elements:

at least 3, 4, 5, 10, 15, 20, 25, 30, 35, preferably all of the following elements: Li, Be, B, F, Na, Mg, Al, P, Cl, K, Ca, Ti, V, Cr, Mn, Fe, Co, Ni, Cu, Zn, Ga, Ge, As, Se, Rb, Sr, Y, Zr, Nb, Mo, Rh, Pd, Ag, Cd, Sn, Sb, Te, I, Ba, Hf, Ta, W, Re, Ir, Hg, TI, Pb, Si, and/or, preferably and at least 3, 4, 5, 8, 12, preferably all of the following elements: La, Ce, Pr, Nd, Pm, Sm, Eu, Dg, Tb, Dy, Ho, Er, Tm, Yb, Lu.

Preferably, the method comprises (or the computer recommends) (a) feeding the animals of the farm or subset, with (solid and/or liquid) isotopic food determined for this farm or subset, or (b) spraying the plants of the farm or field with an isotopic water determined for this farm or field, including determined concentrations of stable isotopes of the following chemical elements:

at least 5, 10, 15, 20, 25, 30, 35, preferably all of the following elements: Li, Be, B, F, Na, Mg, Al, P, Cl, K, Ca, Ti, V, Cr, Mn, Fe, Co, Ni, Cu, Zn, Ga, Ge, As, Se, Rb, Sr, Y, Zr, Nb, Mo, Rh, Pd, Ag, Cd, Sn, Sb, Te, I, Ba, Hf, Ta, W, Re, Ir, Hg, Ti, Pb, Si, at least 5, 8, 12, preferably all of the following elements: La, Ce, Pr, Nd, Pm, Sm, Eu, Gd, Tb, Dy, Ho, Er, Tm, Yb, Lu and/or, preferably and, C, O, N, H, S, said unique code being achieved at the moment of the slaughter of the animal, respectively of the harvest of the plants.

It is possible to describe the following embodiments, with a usage strategy of the elements based on the species and size of the farms so as to be able to guarantee traceability over the long term.

1. Standard intensive poultry farms are characterized by short production cycles (8 cycles×45 d/year approximately) (in organic farming, 5 cycles of 70 d/year approximately) for very large volumes (tens of thousands to hundreds of millions of birds). Trace elements are selected (among Zn, Se, Mo, Si, Ti, Sn, Fe, Cr, Ge, etc.) produced by centrifugation. It is possible to enrich or deplete with isotopes, the latter solution being more favorable from an economic perspective. The isotopic feeding marking cycle will be between 8 to 10 d max.
2. The intensive/extensive farming cycles for large animals (cow, calf, horse, sheep, goat, pigs, etc.) are characterized by long production cycles (11 months, 16 months and more) for large volumes (thousands to millions of individuals). Trace elements are selected (among Zn, Se, Mo, Si, Ti, Sn, Cr, Ge, etc.) produced by centrifugation. It is possible to enrich or deplete with isotopes, the latter solution being more favorable from an economic perspective. The marking cycle will be between 1-3 months toward the end of the animal's life.
3. Farms in fish farming have the same trace elements as for poultry.

The key factors also used are the metabolization and the distribution of the elements as a function of the species (muscles, organs, excrement). The implementations are very important because they guarantee the efficacy of the marking either through the encoding by the animal's food or through the water. This makes it possible to optimize the use and the quantities of stable isotopes required.

It is also possible to describe the following embodiments for the crops as a function of the type and growing location (market, fruit, viticulture, etc.).

1. Market crops in a greenhouse are generally characterized by short cycles between 2-3 months maximum (Standard or Organic) for large volumes (tomatoes, zucchini, beans, etc.). Trace elements are selected (among Zn, Se, Mo, Si, Ti, Mn, Sn, Cr, Ge, Cu, V, etc.) mainly produced by centrifugation and some by Calutron, including Cu, V, Rb.
2. For the other crops, including fruit trees, and everything coming from a plant or tree, trace elements are selected (among Zn, Se, Mo, Si, Ti, Sn, Cr, Ge, rare earth elements REEs, etc.) produced mainly by centrifugation except for the rare earth elements produced via calutrons.

The key factors also selected are the rate of accumulation of the elements and the implementations by dedicated encoding systems.

Based on the enrichment level of the selected isotope, this causes the natural abundance of the other isotopes of a same element to vary. The analysis of the isotopic ratios of a same element will make it possible to show the ratio to be used determining the presence of the marker(s) and its/their concentration value.

With the knowledge of the various isotopic elements and ratios, it is possible to settle for varying (and therefore contributing the corresponding isotope ratios, enriched and/or depleted) the ratios of only 3, 4, 5, 6, 7, 8, 9, 10 elements.

In the present application, spraying means that the plants can be sprayed with the isotopic solution by any standard means, and/or also misted with the isotopic solution and/or submerged in an isotopic solution.

The isotopes can be contributed by any known manner. It is possible to use chlorides, sulfates and oxides. Chlorides and sulfates are generally water-soluble. They can be added to the drinking water or spray water or during the formulation of a solid food. The oxides are generally solid. They can be added to the solid food, but can also be added to the spray water or drinking water.

Preferably, the quantities of isotopes contributed to the animals on the farm or subset are within the limits authorized by the Reference Nutritional Values (RMV) and within the limits of the toxicity values. The computer can therefore be programmed with this information on the RMVs and the limits not to be exceeded in terms of toxicity; it will integrate this data into its recommendations and computations.

Preferably, the quantities of isotopes contributed to the animals of the farm or subset are supplied to the animals taking account of the rate of accumulation (TA) of this or these isotopes in the animal as a function of the farming duration and the feeding period with the isotopic food. As previously seen, the computer can integrate this knowledge of the TA and take it into account as described.

In one embodiment, the animals from the farm or subset are fed exclusively or essentially exclusively with the isotopic food.

Preferably, the animals from the farm or the subset are fed with the isotopic food for at least one subperiod or fraction of the period or farming cycle (e.g., less than ⅓, ¼, ⅕ or ⅙ of the farming or growing cycle). The computer is able to propose an isotopic feeding method that is suitable for the animal or plant species in question, according to criteria able to be recorded in its program.

For example for birds, for example chickens, which have a short breeding duration, the isotopic food is administered at the end of growth, for example between the $11^{th}$ day and the $33^{rd}$ day for slaughter toward the $35^{th}$ day, or between the $24^{th}$ day and the $33/34^{th}$ day (it is generally possible to settle for a marking duration shorter than or equal to 8-10 days).

It is easy to determine the isotopic dietary regimens in order for the code to be present in the animal or plant at the time of slaughter, respectively harvest. This can be done by experimentation, by testing one or several regimens and analyzing the isotopic signature at the time of slaughter, respectively harvest, and preferably by supplying this information to the computer.

The inventive method therefore makes it possible to impose a unique isotopic code on a plant. This plant, with a known isotopic composition, can be used as all or part of a solid isotopic food suitable for a farm or farm subset managed by the model (M) according to the invention. Therefore, in one embodiment of the method for imposing a unique code on a farm or a subset of a farm, the animals are fed on a cycle, according to a suitable predefined regimen, with such a plant, as isotopic solid food or part of an isotopic solid food.

According to the invention, the method making it possible to impose a code specific to the animals of a farm or a subset of a farm, including the products, in particular food products, from or prepared from these animals, this method being suitable for implementing the identification method can comprise feeding the animals of the farm or subset with an isotopic (solid and liquid) food determined for this farm or subset, including determined concentrations of stable isotopes of the following chemical elements:

at least 5, 10, 15, 20, 25, 30, 35, preferably all of the following elements: Li, Be, B, F, Na, Mg, Al, P, Cl, K, Ca, Ti, V, Cr, Mn, Fe, Co, Ni, Cu, Zn, Ga, Ge, As, Se, Rb, Sr, Y, Zr, Nb, Mo, Rh, Pd, Ag, Cd, Sn, Sb, I, Te, Ba, Hf, Ta, W, Re, Ir, Hg, Tl, Pb, at least 5, 8, 12, preferably all of the following elements: La, Ce, Pr, Nd, Pm, Sm, Eu, Gd, Tb, Dy, Ho, Er, Tm, Yb, Lu, and

C, O, N, H, S, said code being finalized at the time of the slaughter of the animal.

The invention also relates to an information recording medium. The recording medium can contain executable instructions programmed to implement a method according to one of the preceding claims when these instructions are executed by an electronic computer.

The invention also relates to an electronic computer for implementing the isotopic identification method according to the invention. This computer can include a programmable logic unit and information recording medium containing software instructions suitable, when they are executed by the logic unit, for implementing steps for comparing a profile of stable isotope concentrations or ratios of a sample from the animal/plant or a product from an animal/plant, in the form of stable isotope concentrations (C2) or ratios (R2), with profiles recorded in the form of unique codes each specific to an animal farm or farm subset or to a farm or field, and determining whether the animal/plant or the product from an animal/plant has a profile substantially equal to a recorded code and therefore indicating the farm or field of origin, or that the animal/plant or the product does not come from any farm or field whose code is registered in the model. Other features of the electronic computer have been described supra.

The computer may further comprise all of the functionalities, devices and programming necessary to perform tasks described here and which are assigned to it:

The computer guarantees the integrity of the unique codes.

The electronic computer receives, as input, results of the concentration analyses (Geochemical passport).

All of the geographical trace elements, ultra traces, macro traces, and trace elements (micros) can be inventoried therein.

The computer also contains the logic and the strategies applicable to the type of farming or growing.

During the determination of the isotopic variations to be done relative to the natural abundance on 1, 2, 3 or more elements, the computer will ensure that the code is not already assigned.

If the code is already assigned and as a function of the logic and the strategies applicable to the type of farming or growing, the computer will perform an additional variation based on a doping index ($+1/1000$, for example) until it finds an available code.

If an availability problem arises, it will first check the differentiation elements of the geochemical passport and account for a value or several values and add them to the recipe of the unique code. This makes it possible in general not to add more than three markers. It is in fact preferable to have at least one signature based on the variation of 3 isotopes.

Once the recipe/unique code is generated, the code is recorded in the computer.

The invention will now be described in more detail using embodiments taken as non-limiting examples and in reference to the appended drawing.

EXAMPLES

Figure 1:
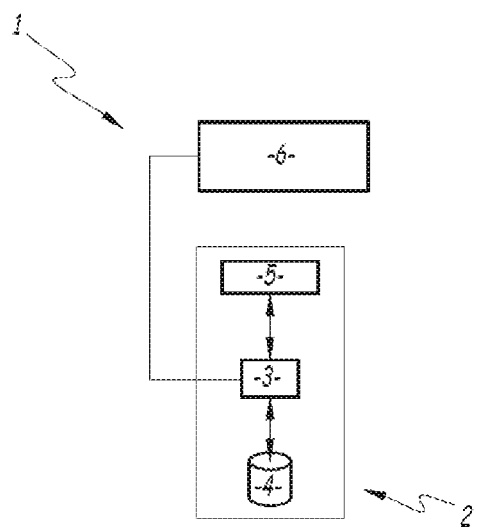
FIG. 1 is a diagram of an assembly with an electronic computer that can be used to carry out the invention.

Example 1: Description of a Computer Assembly for Managing and Defining Isotopic Codes The assembly 1 includes a programmable electronic computer 2, provided with a programmable logic unit 3, an information recording medium 4 and a data exchange interface 5 connected between them by an internal data bus. The electronic computer 2 here also includes a man-machine interface 6.

The unit 3 for example includes a microprocessor or a programmable microcontroller. The medium 4 here includes a memory module, for example using FLASH or EEPROM technology, or a magnetic hard drive. The support 4 contains software instructions suitable for carrying out steps of the method of FIGS. 2 and 3 when these instructions are executed by the computing unit 3.

The man-machine interface 6 here includes a display screen, a data entry tool such as a keyboard and a speaker. In a variant, the man-machine interface 6 can be made differently.

For example, the electronic computer 2 is a microcomputer or a mobile communication device, such as a tablet or telephone. It can also be a remote computer server, accessible through the Internet or a dedicated computer network. In this case, the interface 6 can be omitted and replaced by a dedicated communication interface, for example a computer, a communication device such as a tablet or a television, which performs the same functions as this interface 6 but which is physically separate from the electronic computer 2.

The computer 2 is in particular programmed to implement a predefined model M, for example owing to executable instructions stored in the medium 4.

The model M in particular makes it possible to impose, on the animals or plants, a unique isotopic code specific to a farm or farm subset, respectively farm or field, and optionally even finer granularity levels (e.g., species or varieties, production type, optionally lot), this code being based on the nature, the concentrations or the ratios of stable isotopes of chemical elements. The model (M) further makes it possible, if applicable, to couple a farmed animal or an animal product with a determined farm or farm subset, or a plant or plant product with a determined farm or field, by analyzing concentrations or ratios of stable isotopes, making it possible to determine a concentration or ratio profile of these stable isotopes, in particular by mass spectrometry, and to compare with the unique codes recorded in the model (M).

The data used by the model M can be stored in the medium 4 and/or be stored in a dedicated database accessible by the computer 2.

For example, the interface 5 is suitable for acquiring input data, for example in the form of digital or analog signals or in the form of data structures, such as rate of accumulation values TA and/or measurements of stable isotope concentrations C2 and/or ratios R2. These data can also be transmitted to the computer 2 by means of the interface 6.

Figure 2:
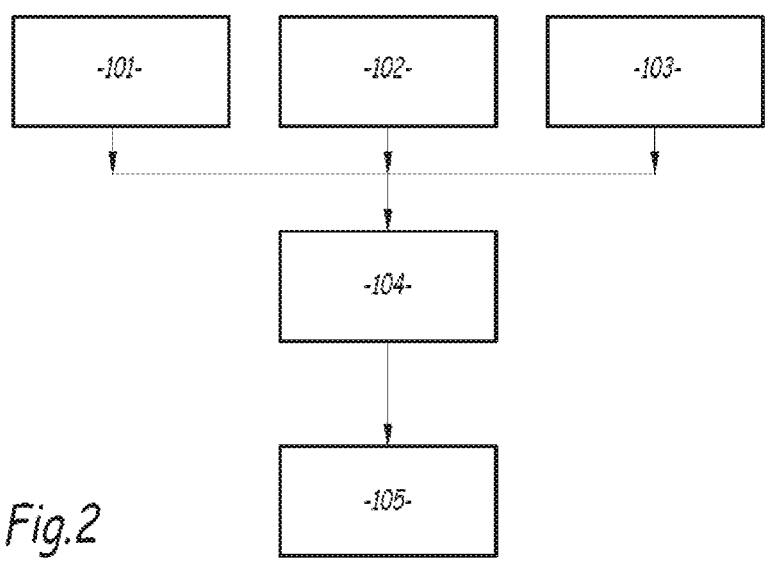
FIG. 2 is a flowchart of a method making it possible to impose a unique code on animals or plants.

FIG. 2, in connection with FIG. 1, schematically describes one embodiment of the method for imposing a unique code. The determination is done, by MS, of the BGS of the farm in step 101, and the data are sent to the computer 2, for example by means of the interface 6.

The TA is known or it can be computed in step 102 by feeding the animals or the plants over a cycle with determined ratios of the stable isotopes of the selected elements, then slaughter or harvest, collecting the flesh and analysis by MS. The data are sent to the computer 2, for example by means of the interface 6.

The computer has the unique codes in memory that have been generated for other farms; this knowledge is identified during a step 103 in FIG. 2.

By increasing the data obtained during steps 101, 102 and 103, the computer generates, during a step 104, a recipe for isotopic food and a dietary regimen that will make it possible to obtain, on this farm, animals or plants having the unique code at the time of slaughter or harvest.

The dietary regimen can be tested and the data kept in the computer 2, for a correlation between this regimen and the obtainment of a ratio of stable isotopes of an element at the time of the slaughter or harvest. Adjustments (in particular in terms of content) can be made in order to obtain usable ratios of isotopes, that is to say, with significant differences measurable by MS at the time of slaughter or harvest.

The computer generates the composition of the isotopic food and/or the dietary regimen, the user being able to access it for example from the interface 6.

In a variant, the dietary regimen can have been determined in advance, and the computer indicates the composition of the isotopic food to the user.

Example 2: Application to a Chicken Farm

Lifecycle of a chicken on the farm: 10 day old chick, $1^{st}$ and second growth phases 21 days, maturity as of the $32^{nd}$ day and slaughter at 45 days, weight between 1.8 and 2.3 kg. The food is specific to each of the 4 phases. The chicks consume an average of 3.5 liters of water over their entire lifetime. The farming cycles follow one another during farming.

Reference will be made to FIGS. 1 and 2.

The BGS of the farm is determined in step 101, and the data are sent to the computer 2, for example by means of the interface 6. Drinking water and solid foods are collected, then analyzed. The ratios of stable isotopes of the following elements (it was possible to determine their presence on the farm, for example by analysis by mass spectrometry (MS) on the water, food, soil, flesh, feathers, bones and/or feet):

these 26 elements: Li, Be, B, F, Na, Mg, Al, Ca, Cr, Mn, Co, Ni, Cu, Zn, Ga, As, Se, Rb, Sr, Mo, Rh, Pd, Ag, Cd, Te, Ba, Ti, Pb, Si, these 15 rare earths: La, Ce, Pr, Nd, Pm, Sm, Eu, Gd, Tb, Dy, Ho, Er, Tm, Yb, Lu.

The MS measurements in the invention in general, and in this example in particular, can be done using the available methods, in particular:

Inductively Coupled Plasma Mass Spectrometry (ICP-MS),

Multicollector-Inductively Coupled Plasma Mass Spectrometer (MC-ICPMS),

Isotope-Ratio Mass Spectrometry (IRMS),

Laser Ablation (LA-ICP/MS),

Laser Induced Breakdown Spectroscopy (LIBS).

The TA is known or it can be computed in step 102 by feeding the animals over a cycle with determined ratios of the stable isotopes of the indicated elements, then slaughter, collecting the flesh and analysis by MS. The data are sent to the computer 2, for example by means of the interface 6.

The computer has the unique codes in memory that have been generated for other farms; this knowledge is identified during a step 103 in FIG. 2.

By increasing the data obtained during steps 101, 102 and 103, the computer generates, during a step 104, a recipe for isotopic food and a dietary regimen that will make it possible to obtain, on this farm, hens having the unique code at the time of slaughter.

The dietary regimen can be tested and the data kept in the computer 2, for a correlation between this regimen and the obtainment of a ratio of stable isotopes of an element at the time of the slaughter at 45 days. Adjustments (in particular in terms of content) can be made in order to obtain usable ratios of isotopes, that is to say, with significant differences measurable by MS at the time of slaughter at about 35 days.

The computer generates the composition of the isotopic food and/or the dietary regimen, the user being able to access it for example from the interface 6.

In a variant, the dietary regimen can have been determined in advance, and the computer indicates the composition of the isotopic food to the user.

For the hens, it is thus possible to define a diet in which the isotopic food constitutes the solid and liquid food for the week leading up to slaughter, step 105.

Example 3: As an Example, on a Chicken, One has

Added $^{86}$Sr to the drinking water over the entire cycle of the animal
Added $^{66}$Zn during the 14 days leading up to slaughter
The MS measurements yielded the following:

| Isotopes | $^{84}$Sr | $^{86}$Sr | $^{87}$Sr | $^{88}$Sr |
|---|---|---|---|---|
| Natural abundance in % | 0.5574 | 9.8566 | 7.0015 | 82.5845 |

| Isotopes | $^{64}$Zn | $^{66}$Zn | $^{67}$Zn | $^{68}$Zn | $^{70}$Zn |
|---|---|---|---|---|---|
| Natural abundance in % | 48.63 | 27.90 | 4.10 | 18.75 | 0.62 |

Example 4: Model Marking on Several Farms Using Different Isotope Ratios

There are 6 farms, farms A, B, C and X with 90,000 hens per cycle, farm D with 300,000 hens per cycle, farm E with 120,000 hens per cycle.

It has been chosen to vary the isotope content levels according to the following table.

| Farm | A | B | C | D | E | X |
|---|---|---|---|---|---|---|
| isotopes | $^{68}$Zn/$^{57}$Fe/$^{95}$Mo | $^{68}$Zn/$^{58}$Fe/$^{95}$Mo | $^{68}$Zn/$^{57}$Fe/$^{95}$Zr | $^{68}$Zn/$^{58}$Fe/$^{87}$Rb | $^{68}$Zn/$^{58}$Fe/$^{95}$Mo | $^{68}$Zn/$^{57}$Fe/$^{46}$Ti |
| Content mg/l production cycle, isotopic beverage for 10 days | 0.344/ 0.049/0.0044 | 0.344/0.0065/ 0.0044 | 0.344/ 0.0049/ 0.00138 | 0.344/ 0.0065/ 0.072 | 0.344/ 0.0065/ 0.00462 | 0.344/ 0.0049/ 0.00528 |

This amounts to producing, for 8 farming cycles per year, in kg:

| $^{68}$Zn | $^{57}$Fe | $^{58}$Fe | $^{95}$Mo | $^{91}$Zr | $^{87}$Rb | $^{46}$Ti |
|---|---|---|---|---|---|---|
| 2.41488 | 0.11907 | 0.029835 | 0.012118 | 0.001125 | 0.1944 | 01004277 |

Example 5: Isotopic Identification of Animals or Plants

This example illustrates the method making it possible to determine whether an animal or plant X comes from a farm belonging to the tracking and identification method according to the invention, and determining its precise origin, namely which farm in the world.

Figure 3:
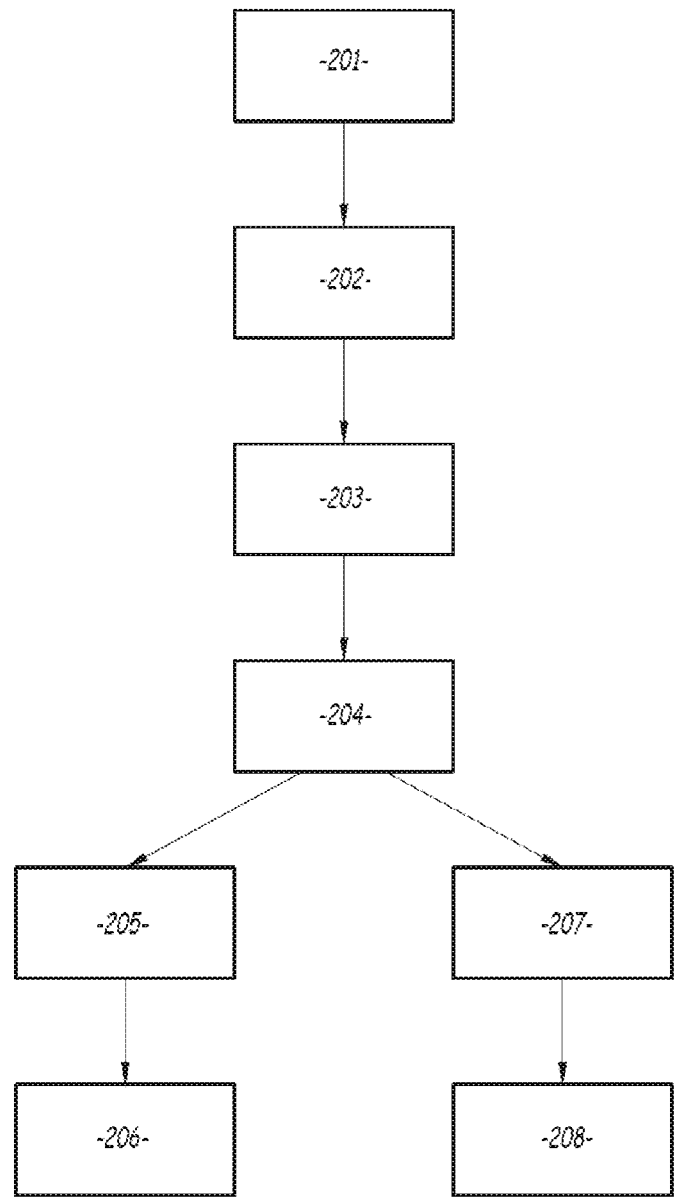
FIG. 3 is a flowchart of a method for isotopic identification of animals or plants, or products therefrom.
Figure 4:
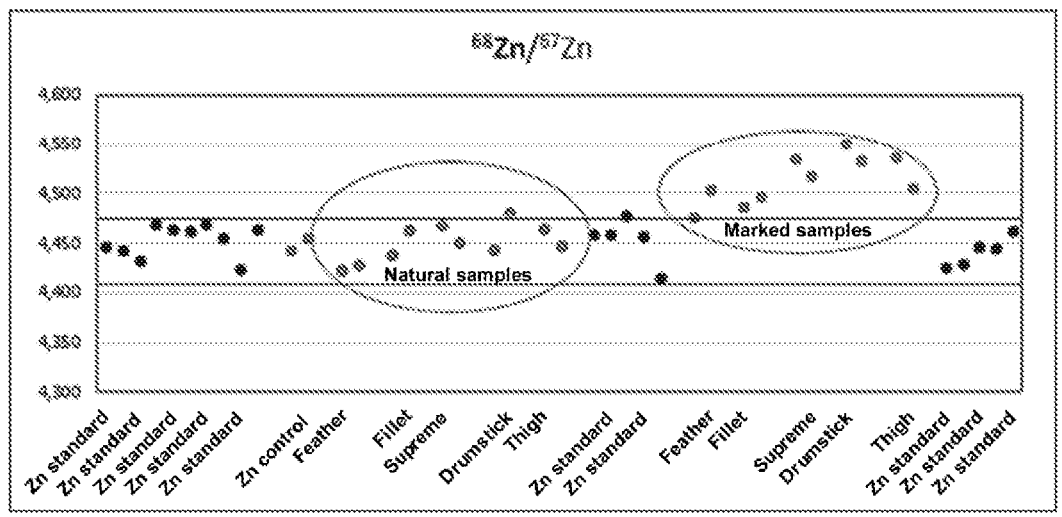
FIGS. 4 to 7 are graphs showing the variations of abundances of isotopes of zinc on natural chickens and isotopic chickens. From left to right: 1/The standard "+control Zn" samples define the values of known natural abundances in light of the studied elements. They constitute a reference with which the marked samples are measured. This in particular makes it possible to determine whether the measuring machine is properly configured and does not have problems related to any contamination. 2/The "natural samples" of feather, supreme fillet, drumstick, thigh are unmarked organic samples of chicken. This makes it possible to check that these chickens are in agreement with the reference. 3/"Standard Zn" is simply there to check any contamination. This is a Quality control. 4/The "marked samples" correspond to the isotopic chickens. 5/"Standard Zn" is simply there to check any contamination. This is a Quality control.
Figure 5:
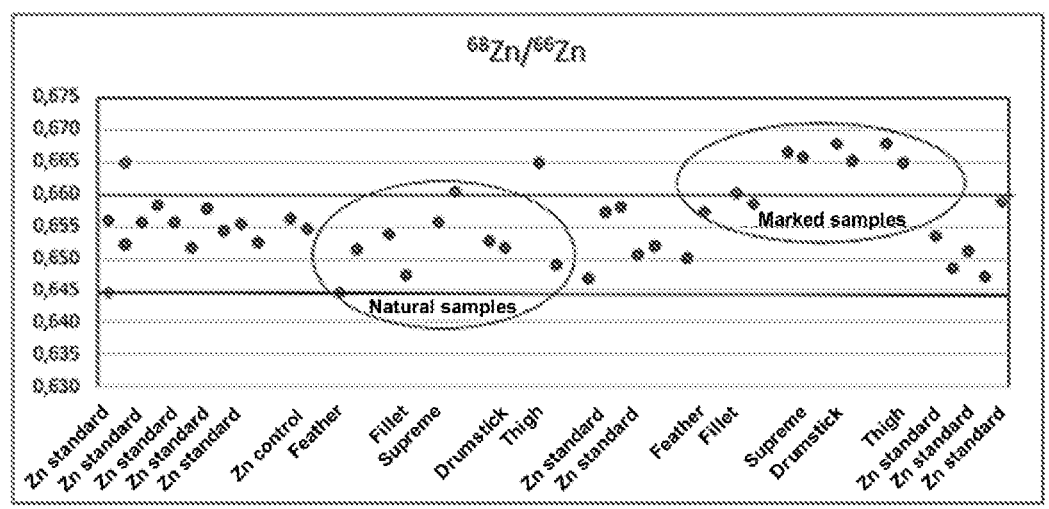
Figure 6:
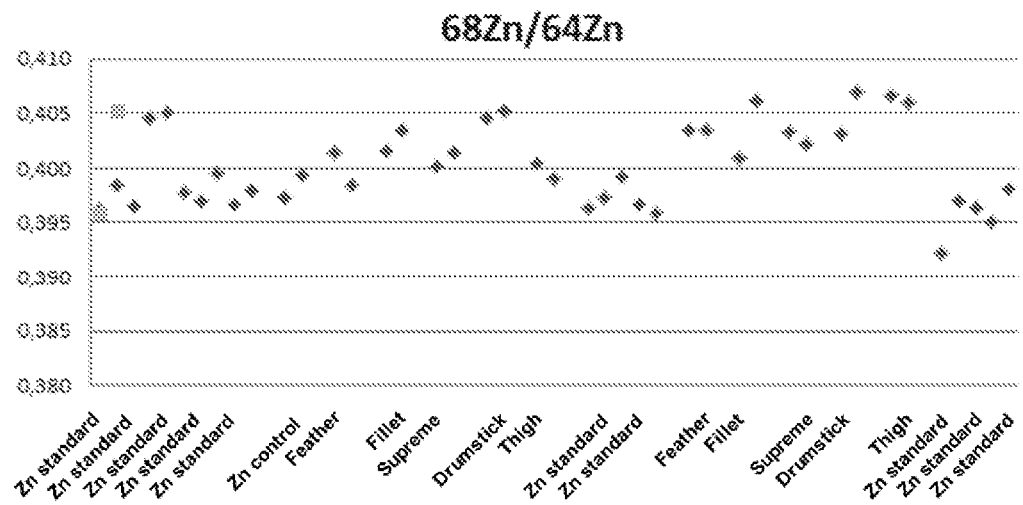
Figure 7:
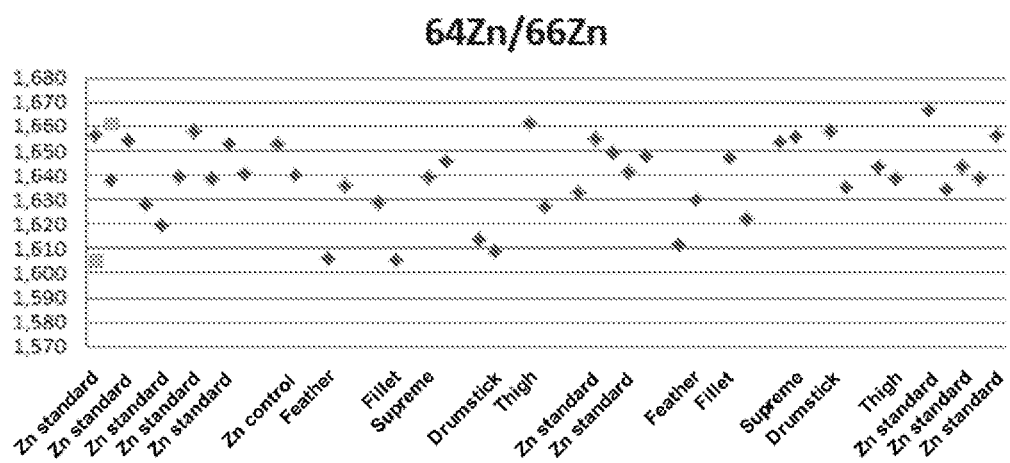

Reference will be made to FIGS. 1 and 3.

A sample of the animal or plant is collected in 201, and subject to MS analyses of all of the elements and their stable isotopes in 202. In 203, the user enters the data from the profile obtained in the computer 2 (or an interface with the mass spectrometer does so automatically, with or without a wired connection), the latter looking in its information recording medium 4 for whether a recorded profile (unique code) is found in the obtained profile, step 204. If there is no correlation (205), the user is informed in 206 that the tested animal or plant does not come from a farm monitored and conditioned according to the invention. If there is a correlation (207), in 208 the computer supplies the user with the precise identity of the farm from which the animal or plant comes.

Example 6: Isotropic Identification of Hens

This example illustrates the method making it possible to determine whether a hen X comes from a farm belonging to the tracking and identification method according to the invention, and determining its precise origin, namely which farm in the world.

Reference will be made to FIGS. 1 and 3.

A sample of flesh is collected in 201, and subject to MS analyses of all of the elements and their stable isotopes in 202. In 203, the user enters the data from the profile obtained in the computer 2 (or an interface with the mass spectrometer does so automatically, with or without a wired connection), the latter looking in its information recording medium 4 for whether a recorded profile (unique code) is found in the obtained profile, step 204. If there is no correlation (205), the user is informed in 206 that the tested animal does not come from a farm monitored and conditioned according to the invention. If there is a correlation (207), in 208 the computer supplies the user with the precise identity of the farm from which the animal comes. The example relates to a whole animal from which a sample has been collected. This animal can for example have been collected from a stall, or a piece of packaged meat sold in pieces can also have been collected. The method also applies in the same way to another animal or to a plant.

Example 7: Internal Marketing of a Unique Code Through the Use of Stable Isotopes of Industrial Broil Chickens The internal unique code corresponds to the ingestion of isotopic markers by industrial broil chickens. This unique code thus corresponds to a controlled variation of the markers in the entire body of the chicken.

These variations are imposed by the quantity of markers ingested by the chicken. These quantities, for a same unique code, must be adjusted as a function of certain environmental criteria:
 The farming conditions of the industrial broil chickens
 The ingestion route of the markers
 The metabolization of these markers by the body of the industrial broil chickens Under industrial conditions, the broil chickens are raised in a closed building, heated to between 30 and 20° C., and under artificial light for 23 to 18 hours. The chicks arriving in the building are raised until the age of 35 to 42 days to an average weight between 1.8 and 2.2 kg. The information is compiled in Table 1:

| 1: Farming conditions of industrial broil chickens of strain ROSS 308 (Manual management of ROSS broil chickens, Aviagen, 2010) | | | | | |
|---|---|---|---|---|---|
| Cycle (days) | Temperature (° C.) | Brightness (hours/day) | Cumulative food consumption (g) | Cumulative water consumption (mL) | Average live weight/ chicken (g) |
| 1 | 30 | 23 | 13 | 28 | 57 |
| 6 | 27 | 23 | 131 | 275 | 160 |
| 15 | 24 | 20-18 | 613 | 1124 | 535 |
| 21 | 22 | 20-18 | 1183 | 2055 | 929 |
| 27 | 20 | 20-18 | 1968 | 3357 | 1414 |
| 35 | 20 | 20-18 | 3322 | 5716 | 2144 |
| 42 | 20 | 20-18 | 4741 | 8213 | 2809 |

The ingestion route of the markers can be through water or food. In each of the cases, the quantity of markers to be contributed is computed as a function of the concentration of the markers initially present in the water and food. Another important factor to compute the quantity of markers to be ingested is the metabolization/absorption by the body of the chicken.

Let us take the example of the case of zinc as marker for fixed conditions. It will be added for 10 days, from the $24^{th}$ to the $33^{rd}$ days, through the drinking water or the food. The chicken will eat about 1.5 kg of food, the zinc concentration of which is 85 mg/kg. It will drink about 2.6 L of water, the zinc concentration of which is about 9 µg/L. The total quantity of zinc ingested during this period will be 127.73 mg.

Zinc has 5 stable isotopes, the natural abundances of which are listed in Table 2. Let us choose as marker to add zinc 68, the natural abundance of which is 18.75%. The total quantity of zinc 68 contributed through the food and water is therefore 23.95 mg (18.75%*127.7 mg). The quantity to be added depends on the selected target value: in this example, it is 10% of the ratio $^{68}Zn/^{64}Zn$. It is computed according to equation (1) as a function of the abundances of each isotope.

In the case of a complete homogenization of the natural zinc and the marker, a modified average abundance of zinc 68 of 18.907% will then be necessary for an addition of 0.25 mg spread out over ten days. In the case where the marker is more or less well metabolized by the chicken than the natural zinc, the quantity of markers to be added will be recalculated downward or upward, respectively.

| 2: Natural abundances of the isotopes of zinc. | | | | | |
|---|---|---|---|---|---|
| Isotopes of zinc | 64 | 66 | 67 | 68 | 70 |
| Natural abundances | 48.63% | 27.90% | 4.10% | 18.75% | 0.62% |

$$\text{Target value} = \left[ \frac{(^{68}Zn/^{64}\text{Modified})_{Zn}}{(^{68}Zn/^{64}\text{Natural})_{Zn}} - 1 \right] * 1000 \quad \text{(Equation 1)}$$

Example 8: Test on a Chicken Farm

The isotopic marking of a quantity of chickens was tested, grouped into different lots. Our experiment consisted of adding isotopic markers into the drinking water and/or the food of these chickens so that they are marked in vivo. The concentrations and the marking periods (cycles) varied for the different lots as a function of the applied test scenarios. The chickens were next killed, cut into pieces and analyzed for compositions in terms of concentrations and isotopes done in order to quantify and evaluate the marking. This made it possible to show the metabolization phase of the markers in the body of the chickens. The presence and the durability of the markers were also studied by analyzing organic samples.

Identical farming conditions for the different lots (excluding markers)
Closed environment (battery on hard soil type)
Chickens of fast-growing breed (ROSS 308)
Food produced all at once for the different lots (homogeneity)
Lifetime of the chickens from 35 to 42 days (1.8 to 2.2 kg)
1. Farming Conditions
a. The Hen House The henhouse is made in a garden shed, in order to simulate intensive farming conditions. Four enclosures were built in order to be able to conduct four tests at once. Each enclosure measures 0.72 m² (0.8 m*0.9 m). According to the laws on intensive farming, it is possible to place 12 to 15 chickens/m², weighing 2.2 to 1.8 kg each, respectively. It is therefore possible to place up to 8 chickens per enclosure. Let us consider a maximum of 5 chickens per half-enclosure in order to account for the well-being of the animals.

b. Management of the Chicks and Chickens

The fast-growing ROSS 308 chicks come from Couvoir Duc, Quartier des Blaches, Crest, 26400. They are available with chick sexing.

The chicks are raised in an enclosure on the ground. Boxes are placed on the ground and the bedding is made up of wood shavings. It is replaced every other day for sanitary reasons. The enclosure is equipped with a water trough suitable for chicks (and chickens) and a feed trough. The necessary heat is produced by an infrared bulb suitable for poultry. The chicks need a temperature around 35° C. for the first few days, which should decrease to around 20° C. (Table 3).

The chickens are next distributed into their respective enclosures several days before the beginning of the tests. Each enclosure is equipped with a feed trough and a water trough with nipples. The ground is covered with a PVC floor and bedding made up of wood shavings. It is replaced every other day for sanitary reasons.

TABLE 3

| Cycle (days) | Ideal temperature (° C.) | Date | T (° C.) morning | T (° C.) Afternoon | Mortality | IR bulb (day) |
|---|---|---|---|---|---|---|
| 1 | 30 | Aug. 29, 2017 | | 40 | | yes |
| 2 | | Aug. 30, 2017 | | 28 | 1 | yes |
| 3 | 28 | Aug. 31, 2017 | 26 | | | yes |
| 4 | | Sep. 01, 2017 | 27 | | | yes |
| 5 | | Sep. 02, 2017 | 27 | | | yes |
| 6 | 27 | Sep. 03, 2017 | | 30 | 1 | yes |
| 7 | | Sep. 04, 2017 | 16 | | 1 | yes |
| 8 | | Sep. 05, 2017 | 16 | | | yes |
| 9 | 26 | Sep. 06, 2017 | 16 | | 1 | yes |
| 10 | | Sep. 07, 2017 | 14.5 | | | yes |
| 11 | | Sep. 08, 2017 | 14 | | | yes |
| 12 | 25 | Sep. 09, 2017 | 14 | | | yes |
| 13 | | Sep. 10, 2017 | 13 | | | yes |
| 14 | | Sep. 11, 2017 | 15 | | | yes |
| 15 | 24 | Sep. 12, 2017 | 15 | | | yes |
| 16 | | Sep. 13, 2017 | 14 | | | yes |
| 17 | | Sep. 14, 2017 | 15 | | | yes |
| 18 | 23 | Sep. 15, 2017 | 17 | | | no |
| 19 | | Sep. 16, 2017 | 14 | | | No |
| 20 | | Sep. 17, 2017 | 14 | | | No |
| 21 | 22 | Sep. 18, 2017 | 13 | | | no |
| 22 | | Sep. 19, 2017 | | | | No heating |
| 23 | | Sep. 20, 2017 | | | | No heating |
| 24 | 21 | Sep. 21, 2017 | | | | No heating |
| 25 | | Sep. 22, 2017 | | | | No heating |
| 26 | | Sep. 23, 2017 | | | | No heating |
| 27 | 20 | Sep. 24, 2017 | | | | No heating |
| 28 | | Sep. 25, 2017 | | | | No heating |
| 29 | | Sep. 26, 2017 | | | | No heating |
| 30 | | Sep. 27, 2017 | | | | No heating |
| 31 | | Sep. 28, 2017 | | | | No heating |
| 32 | | Sep. 29, 2017 | | | | No heating |
| 33 | | Sep. 30, 2017 | | | | No heating |
| 34 | | Oct. 01, 2017 | | | | No heating |
| 35 | 20 | Oct. 02, 2017 | | | | No heating |
| 36 | | Oct. 03, 2017 | | | | No heating |
| 37 | | Oct. 04, 2017 | | | 8 (marked) | No heating |
| 42 | | Oct. 09, 2017 | | | 4 (controls) | No heating |

2. Experimental Conditions

During a cycle, up to 3 different marking tests and 1 control test without marking can be done. The lots can be 5 chickens each.

The test parameters to be varied are:
The marking duration: 10, 20, 35, 42 days, etc.
The mode of administration: drinking water or food
The concentration and the intensity of the markers
Different breeds of chickens: fast and slow growth, etc.
The choice of markers 3. Cycle 1 a. Experimental Conditions of Cycle 1:

First, the tests of cycle 1 are done on ROSS 308 fast-growing chickens, through the drinking water and for 10 days (24 to 34 days, Lot 1) and 15 days (19 to 34 days, Lot 2). The marked chickens were ultimately killed early in the morning on the 37$^{th}$ day. The "control" chickens were killed on day 42.

Among the 20 chicks in the experiment, a first lot is considered to be the "control" and is not marked. A second and third lot are marked at 30 per mil (Table 4). The quantity of chickens per lot will depend on the mortality rate. The mortality is four chicks. Four chickens are distributed for each test.

TABLE 4

Experimental conditions for Cycle 1. By default, lot 1 of each cycle will be the control lot without marking.

| | Chickens | Nb | Period (days) | Markers | Marking | Marking vector |
|---|---|---|---|---|---|---|
| Cycle 1—Lot 1 | ROSS 308 | 4 | 24-34 | $^{57}$Fe, $^{68}$Zn | 30/1000 | Drinking water |
| Cycle 1—Lot 2 | ROSS 308 | 4 | 19-34 | $^{57}$Fe, $^{68}$Zn | 30/1000 | Drinking water |
| Cycle 1—Lot 3 | ROSS 308 | 4 | — | — | None | — |

The chicken food consists of corn, soy extract feedstock cake, wheat, hulled sunflower extract feed cake, bran, soybean oil, calcium carbonate, salt, magnesium oxide, monocalcium phosphate and a premix of additives.

TABLE 5

Composition of the food for chicks and chickens in cycle 1.

| Composition | Formulation | Concentration (photo) | Concentration (cycle 1, bag 1) | Concentration (cycle 1, bag 2) |
|---|---|---|---|---|
| Guarantee | | | 08/29/2017 | 09/25/2017 |
| Crude protein | | 19.70% | 19.60% | 19.60% |
| Crude fat | | 2.70% | 2.70% | 2.70% |
| Raw ash (M. Miner.) | | 5.40% | 5.70% | 5.70% |
| Crude cellulose | | 4.20% | 4.20% | 4.20% |
| Calcium | | 0.90% | 1.05% | 1.05% |
| Phosphorus | | 0.55% | 0.55% | 0.55% |
| Sodium | | 0.13% | 0.15% | 0.15% |
| Methionine | | 4.60 g/kg | 4.80 g/kg | 4.80 g/kg |
| Lysine | | 10.70 g/kg | 10.80 g/kg | 10.80 g/kg |
| Additives (not guaranteed, minimum) | | | Ratio 1.15-1.2 | Ratio 1.15-1.2 |
| Vitamins | | | | |
| A | | 8600 Ul/kg | 10000 Ul/kg | 10000 Ul/kg |
| D3 | | 2600 Ul/kg | 3000 Ul/kg | 3000 Ul/kg |
| E | Alpha-tocopheryl acetate | 30 Ul/kg | 35 Ul/kg | 35 Ul/kg |
| C | | 5 mg/kg | 6 mg/kg | 6 mg/kg |
| Oligo-elements | | | | |
| Iron E1 | $FeSO_4 \cdot H_2O$ | 50 mg/kg | 58 mg/kg | 58 mg/kg |
| Copper E4 | $CuSO_4 \cdot 5H_2O$ | 12 mg/kg | 14 mg/kg | 14 mg/kg |
| Manganese E5 | MnO | 78 mg/kg | 91 mg/kg | 91 mg/kg |
| Zinc | ZnO | 75 mg/kg | 87 mg/kg | 87 mg/kg |
| Iodine | KI | 0.90 mg/kg | 1 mg/kg | 1 mg/kg |
| Selenium | $Na_2SeO_3$ | 0.30 mg/kg | 0.35 mg/kg | 0.35 mg/kg |
| Enzymes | | | | |
| 6-Phytase EC 3, 1, 3, 26 | | 375 OTU/kg | 440 OTU/kg | 440 OTU/kg |
| Endo-1, 3 (4)-beta-glucanase EC 3, 2, 1,6 | | 1500 UV/kg | 1750 UV/kg | 1750 UV/kg |
| Endo-1, 4-beta-xylanase EC 3, 2, 1,8 | | 1100 UV/kg | 1285 UV/kg | 1285 UV/kg |
| Antioxidants | | | | |
| Propyl gallate E310 | | 4 mg/kg | 4 mg/kg | 4 mg/kg |
| BHT E321 | | 9 mg/kg | 11 mg/kg | 11 mg/kg | b. Formulation of the Marking of Cycle 1

We have chosen iron and zinc as marking elements, with their associated isotopes: $^{57}Fe$ and $^{68}Zn$. These elements are two oligo-elements whose content levels in food are generally between 80 and 150 µg/g and 40-120 µg/g, respectively. In the food that is given to the chickens, the minimum concentration of iron is 50 µg/g and of zinc is 75 µg/g.

In order to calculate the quantity of markers to be added in the drinking water and considering a metabolization of 100%, we based ourselves on the iron and zinc concentration measured in the food of a premix producer for poultry, or 144 µg/g of iron and 120 µg/g of zinc (Table 4).

For lot 2, 500 mL of parent solution was prepared in a bottle. For lot 3, 750 mL of parent solution was prepared in another bottle. Each day, a volume of these parent solutions (50 mL) is withdrawn and diluted in a volume of water.

The parent solution must have a pH below 2.5 in order to avoid the precipitation of the iron. To that end, nitric acid will be added: the quantity to be added depends on the initial pH of the parent solution.

The daily water consumption for 4 chickens will evolve from 730 mL to 1.44 L from the $19^{th}$ to the $33^{rd}$ day (calculated with a 10% margin). By diluting 50 mL of the parent solution to achieve these volumes of water, the dilution rate is between 5 and 3.3% (Tables 5 and 6). The iron and zinc concentrations in the drinking water are below the recommended values of 0.3 mg/L and 5 mg/L, respectively (Tables 6 and 7).

TABLE 6

Quantity of markers to be added in the drinking water to have a marking of 5, 10 and 30 per mil (considering 100% metabolization) over 10 days.

| | Marking 30/1000 $24^{th}$ to $34^{th}$ days | | Marking 30/1000 $19^{th}$ to $34^{th}$ days | | Weighing precision (Without cup) |
|---|---|---|---|---|---|
| $^{57}Fe$ 95.5% | $^{57}Fe$ | $^{57}FeCl_2$ | $^{57}Fe$ | $^{57}FeCl_2$ | |
| 1 chicken/day | 15.00 µg | 33.68 µg | | | |
| 1 chicken/10 days | 150.00 µg | 336.80 µg | | | |

TABLE 6-continued

Quantity of markers to be added in the drinking water to have a marking of 5, 10 and 30 per mil (considering 100% metabolization) over 10 days.

| | Marking 30/1000 24$^{th}$ to 34$^{th}$ days | | Marking 30/1000 19$^{th}$ to 34$^{th}$ days | | Weighing precision (Without cup) |
|---|---|---|---|---|---|
| 4 chickens/day | 60 µg | 134.72 µg | | | |
| 4 chickens/10 days | 600.00 µg | 1347.2 µg | | | 93.1% |
| 4 chickens/day | | | 60 µg | 134.72 µg | |
| 4 chickens/15 days | | | 900 µg | 2020.8 µg | |
| $^{68}$Zn 97.8 % | $^{68}$Zn | $^{68}$ZnCl$_2$ | $^{68}$Zn | $^{68}$ZnCl$_2$ | |
| 1 chicken/day | 105 µg | 214.61 µg | | | |
| 1 chicken/10 days | 1050 µg | 2146.10 µg | | | |
| 4 chickens/day | 420 µg | 858.43 µg | | | |
| 4 chickens/10 days | 4200 µg | 8584.30 µg | | | 98.7% |
| 4 chickens/day | | | 420 µg | 858.43 µg | |
| 4 chickens/15 days | | | 6300 µg | 12876.5 µg | |

TABLE 7

Theoretical chemical data on the iron and zinc concentration in the parent solutions and drinking water (diluted) of Cycle 1.

| | Marking 30/% 1000 | Solution |
|---|---|---|
| $^{57}$FeCl$_2$ (g) | 0.0017234 | Parent |
| $^{57}$FeCl$_2$ (mol) | 1.34809E−05 | Parent |
| $^{57}$FeCl$_2$ (mol/L) | 2.69618E−05 | Parent |
| $^{57}$FeCl$_2$ (mg/L) | <0.17 | Diluted |
| $^{68}$ZnCl$_2$ (g) | 0.00766 | Parent |
| $^{68}$ZnCl$_2$ (mol) | 5.51751E−05 | Parent |
| $^{68}$ZnCl$_2$ (mol/L) | 0.00011035 | Parent |
| $^{68}$ZnCl$_2$ (mg/L) | <0.77 | Diluted |

TABLE 8

Dilution of a volume of parent solution in a volume of water during the 10 days of marking of Cycle 1

| Jour | Date | Volume of parent solution | Volume of water/4 chickens (as close as possible) | Lot 1 | Lot 2 | Notes |
|---|---|---|---|---|---|---|
| 19 | Sun. Sep. 17, 2017 | 50 ml | 685 g | | no | |
| 20 | Mon. Sep. 18, 2017 | 50 ml | 731 g | | no | |
| 21 | Tue. Sep. 19, 2017 | 50 ml | 777 g | | no | |
| 22 | Wed. Sep. 20, 2017 | 50 ml | 823 g | +10 g | no | |
| 23 | Thu. Sep. 21, 2017 | 50 ml | 874 g | | no | |
| 24 | Fri. Sep. 22, 2017 | 50 ml | 925 g | | | |
| 25 | Sat. Sep. 23, 2017 | 50 ml | 976 g | | | |
| 26 | Sun. Sep. 24, 2017 | 50 ml | 1031 g | | | |
| 27 | Mon. Sep. 25, 2017 | 50 ml | 1087 g | | | |
| 28 | Tue. Sep. 26, 2017 | 50 ml | 1142 g | | | |
| 29 | Wed. Sep. 27, 2017 | 50 ml | 1193 g | | | |
| 30 | Thu. Sep. 28, 2017 | 50 ml | 1244 g | | | |
| 31 | Fri. Sep. 29, 2017 | 50 ml | 1295 g | | | |
| 32 | Sat. Sep. 30, 2017 | 50 ml | 1341 g | | | |
| 33 | Sun. Oct. 01, 2017 | 50 ml | 1387 g | | | |
| 34 | Mon. Oct. 02, 2017 | — | — | no | no | |
| 35 | Tue. Oct. 03, 2017 | — | — | no | no | |
| 36 | Wed. Oct. 04, 2017 | — | — | no | no | Slaughter 8 chickens marked lot 1 and 2 |
| 42 | Mon. Oct. 09, 2017 | — | — | | | Slaughter 8 control chickens |

Each day and for both enclosures corresponding to the "marked" chickens, the appropriate dilutions are prepared.

c. Results

Placement in Solution of the Markers

The two parent solutions have a concentration of 3.4 mg/L of $^{57}Fe$, as well as of 17.6 and 19.4 mg/L of $^{68}Zn$. From these data, the potential-pH diagram of the iron was calculated to check the solubilization of the iron (FIG. 1). The red dots correspond to the pH of the drinkable solutions given to the chickens, diluted from the parent solutions.

$$C(^{57}Fe)=((0.17/1000)*57)/(0.685+0.05)=0.01318 \text{ M}.$$

The concentration in $^{57}Fe$ of 0.17 mg corresponds to the quantity in 50 mL of parent solution.

$C_1$ $(HNO_3)=(50*0.335)/(685+50)=0.023$ M. The least diluted solution. $pH_1=1.642$ $C_2$ $(HNO_3)=(50*0.335)/(1387+50)=0.012$ M. The most diluted solution. $pH_1=1.933$ The concentration in $HNO_3$ of 0.335 M corresponds to 250 mL of solution 1 (pH=1)+750 ml of solution 2 (pH=0.3) having a pH of 0.475.

The iron must not have precipitated in the diluted solutions given to the chickens to drink because the pH is lower than 2 and stays in the range of $Fe^{3+}$.

TABLE 9

Sampling by lot of Cycle 1

| Day | Food | Water | Parent sol. | Droppings | Meat/bone | Bedding |
|---|---|---|---|---|---|---|
| 1-18 | ✓ | ✓ | | | | ✓ |
| 19 | | | ✓ | | | |
| 20 | | | | | | |
| 21 | | | | | | |
| 22 | | | | ✓ | | |
| 23 | | | | | | |
| 24 | ✓ | ✓ | ✓ | ✓ | | |
| 25 | | | | | | |
| 26 | | | | ✓ | | |
| 27 | | | | | | |
| 28 | | | | ✓ | | |
| 29 | | | | | | |
| 30 | | | | ✓ | | |
| 31 | | | | | | |
| 32 | | | | ✓ | | |
| 33 | | | | | | |
| 34 | | | | | | |
| 35 | | | ✓ | | ✓ | ✓ |
| Number | 2 * 2 = 4 | 2 | 3 | 6 * 3 = 18 | 3 * 12 = 36 | | d. Results of Analyses of the Obtained Markers:

For the doping of the Zinc: $Zn^{68}$ by comparing the abundance of the stable isotopes. As a reminder, the calculated isotopic ratios are:

| Ratios | Min | Max |
|---|---|---|
| 68Zn/67Zn | 4.416 | 4.482 |
| 68Zn/66Zn | 0.645 | 0.665 |
| 68Zn/64Zn | 0.396 | 0.405 |
| 64Zn/66Zn | 1.605 | 1.661 |

We note that the samples of marked meat have an abundance value higher than the known standard. FIGS. 4-7.

For the doping of the Iron: $Fe^{57}$ by comparing the abundance of the stable isotopes. As a reminder, the calculated isotopic ratios are:

| Ratios | Min | Max |
|---|---|---|
| 57Fe/56Fe | 0.0224 | 0.2330 |
| 58Fe/56Fe | 0.3664 | 0.00 |
| 58Fe/57Fe | 16.5406 | 0.00 |

Figure 8:
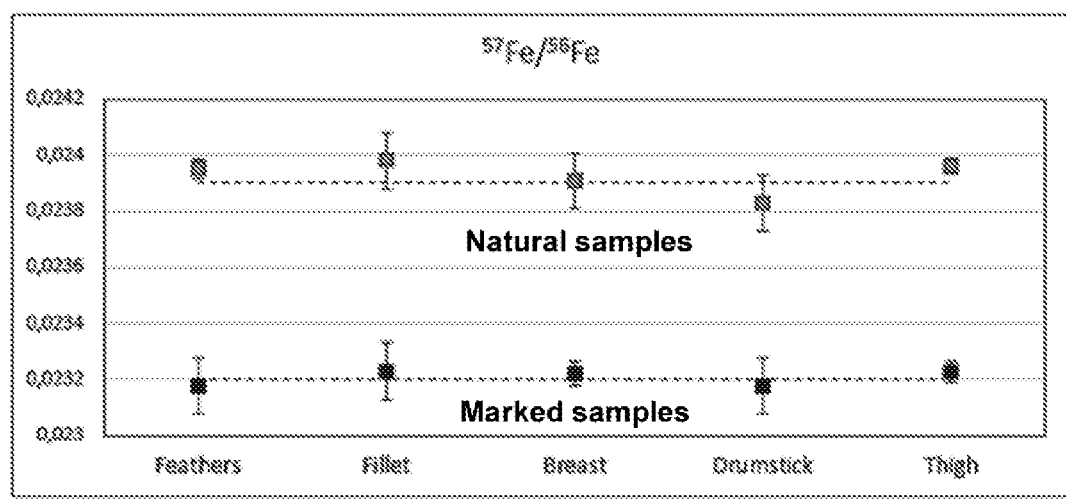
FIG. 8 is a graph showing the signature differences between isotopic chicken samples and natural chicken samples.

We note that the samples of marked meat have an abundance value higher than the known standard. FIG. 8.

Although the doping had been done on Zn68, the variation of the abundance is not measurable with respect to the most abundant isotope. This shows that our markers are in an infintesimal quantity and that it is important the measure the correct isotopic ratio in order to detect the markers.

During the experiment, we continually tried to find the minimum quantity to be ingested by the animals (the poultry). In light of the doping and the natural abundance of the isotope that will be selected, certain isotopic ratios are more indicative of the caused isotopic variation, thus determining the unique code. This is why we must look first and foremost at the Zn68/Zn67 ratio.

What is claimed is:

1. An isotopic identification method for coupling a farmed animal or an animal product with a determined farm or farm subset, or a plant or plant product with a farm or field, by analyzing the concentration or ratios of chemical elements and of stable isotopes of several chemical elements, said method comprising:
   a) obtaining a sample derived from the farmed animal or animal product or the plant or plant product to be identified, measuring the concentration or ratios of chemical elements and of stable isotopes;
   b) obtaining a measured profile of concentration or ratios of said chemical elements and stable isotopes;
   c) providing an electronic computer including a programmable logic unit and information recording medium and/or a database accessible to the computer, wherein
      (i) said electronic computer generates unique codes specific to registered farms or farm subset, or to several fields, each unique code being a profile of concentration or ratios of chemical elements and of stable isotopes of several chemical elements, and the electronic computer and/or the database stores these unique codes,
      (ii) said electronic computer computes and proposes new unique codes and isotope variations for each new farm or new farm subset, or to each new field, based on computer's knowledge of the already generated and stored unique codes,
      (iii) said electronic computer and/or the database stores the unique codes generated by the electronic computer; and
      (iv) said electronic computer further comprises a man-machine interface or communication interface; and
   d) entering the profile measured in a) into the electronic computer provided in c) through the man-machine interface or communication interface,
      wherein said electronic computer further comprises software instructions suitable, when they are executed by the logic unit, for:
      (i) comparing said entered profile of concentration or ratios with said unique codes generated by said computer and stored in said computer or database; and
      (ii) concluding that the animal/plant or the product from an animal/plant to be identified has a measured profile equal to one of the unique codes generated by and stored, thus indicating the animal farm/farm or field of origin in response to determining that, at the end of the comparison, the measured profile of concentration or ratios corresponds to a stored unique code and the animal or plant, or part thereof, contains said unique code, and otherwise, concluding that the animal/plant or the product does not come from any animal farm/farm or field whose code is stored in the electronic computer or database; and wherein measuring the concentration or ratios of chemical elements and of stable isotopes of chemical elements is carried out by mass spectrometry; and e) using the measured profile of concentration or ratios obtained from said method to determine whether the animal/plant or the product from which the sample was obtained does or does not come from any animal farm/farm or field whose code is stored in the electronic computer or database.

2. The method according to claim 1, wherein a) comprises measuring the concentration of:
  stable isotopes of at least 5 of the following elements: Li, Be, B, F, Na, Mg, Al, P, Cl, K, Ca, Ti, V, Cr, Mn, Fe, Co, Ni, Cu, Zn, Ga, Ge, As, Se, Rb, Sr, Y, Zr, Nb, Mo, Rh, Pd, Ag, Cd, Sn, Sb, Te, I, Ba, Hf, Ta, W, Re, Ir, Hg, Ti, Pb, Si,
  stable isotopes of at least 5 of the following elements: La, Ce, Pr, Nd, Pm, Sm, Eu, Gd, Tb, Dy, Ho, Er, Tm, Yb, Lu, and
  at least two chemical elements selected from the group consisting of C, O, N, H, and S.

3. The method according to claim 1, wherein the electronic computer or the database comprises the unique codes of animals or plants of specific farms or fields, defined by the concentration or ratios of chemical elements and of stable isotopes of one or several of the following chemical elements as they are measured at the time of the slaughter/harvest in the animals from these specific farms or fields:
  stable isotopes of at least 5 of the following elements: Li, Be, B, F, Na, Mg, Al, P, Cl, K, Ca, Ti, V, Cr, Mn, Fe, Co, Ni, Cu, Zn, Ga, Ge, As, Se, Rb, Sr, Y, Zr, Nb, Mo, Rh, Pd, Ag, Cd, Sn, Sb, Te, I, Ba, Hf, Ta, W, Re, Ir, Hg, Ti, Pb, Si,
  stable isotopes of at least 5 of the following elements: La, Ce, Pr, Nd, Pm, Sm, Eu, Gd, Tb, Dy, Ho, Er, Tm, Yb, Lu and,
  at least two chemical elements selected from the group consisting of C, O, N, H, and S.

4. The method according to claim 3, wherein said unique code for an animal farm or a plant farm or field has been determined by the electronic computer and imposed on the animals from the farm or the plants from the farm or field by said isotopic food distributed such that this code is integrated by the animal when it is slaughtered or the plant when it is harvested.

5. The method of claim 1, wherein each unique code has been imposed to animals of a farm or a subset of a farm, or to plants of a farm or a field, or to products from said animals or plants, by a method using said electronic computer, said method comprising:
  i—determining the concentration or ratios of chemical elements and stable isotopes of several chemical elements in water and/or food used in the farm and/or in flesh, or in skin and/or bones of said farm animals of at least one farming cycle in advance of 2i below, or in the spray water for the growing and/or in the plant from at least one growing cycle in advance of 2i below, said concentration or ratios of chemical elements and stable isotopes of several elements constituting a basal geochemical signature (BGS) of the farm or the farm subset, or of the farm or the field, having the BGS stored in the electronic computer or the database; and
  2i—having the electronic computer:
  select at least one element having stable isotopes among those present in the BGS, and consider the concentration or ratios of these stable isotopes;
  take into account (a) of the accumulation rate of said isotopes in said animals or plants, (b) the BGS of i—, and (c) the unique codes of other farms or fields, (a), (b) and (c) being stored in the electronic computer or the database, and
  determine a diet for an animal or plant, with an isotopic food comprising determined ratios of said isotopes, and suitable to impart, at the moment of the slaughter of the animal or harvest of the plant and in light of the BGS of the farm or the crop, a unique code to said animals or plants from this farm, or said crop differing from any other unique codes of other farms or fields stored in the computer or the database; and
  3i—providing said animals or plants from this cycle, or animals or plants of another farming or growing cycle with said diet and isotopic food comprising a determined ratio of said isotopes, and imparting their unique code to the animals or plants fed with this diet and isotopic food.

6. The method according to claim 5, wherein i further comprises analyzing in advance of 2i the ratios of stable isotopes of several chemical elements in the flesh, skin, and/or bones of said animals from the farm, or in the tissues of plants, and/or analyzing the ratios of stable isotopes of several chemical elements in the water and food used for consumption by the animals or plants, and obtaining based on said analysis the BGS of the farm or the farm subset.

7. The method according to claim 5, wherein 2i further comprises providing the animals with the isotopic food during a determined period so as to obtain, at the time of slaughter, animals having acquired the unique code specific to the farm or the farm subset.

8. The method according to claim 5, further comprising after i and 2i, during a farming or growing cycle, analyzing at least once the water and/or food in order to detect a potential variation in the concentration of the stable isotopes of the selected chemical elements.

9. The method according to claim 5, further comprising using an electronic computer in which are stored (a) the unique codes specific to animal farms or farm subsets, or to other farms or fields, these unique codes having been previously determined and recorded, and/or (b) said BGS of the farm or farm subset, or the farm or field.

10. The method according to claim 9, wherein the computer stores data of said animals of the farm or subset, or said plants, as a function of the farming and respective growing conditions, and said computer comprises a computer program or an algorithm so as to establish a correlation between a variation in concertation of isotope elements and the feeding diet with the isotopic food, in order to obtain a unique code of the time of slaughter or harvest.

11. The method according to claim 9, wherein the computer is equipped with a computer program or an algorithm so as to allow, from said BGS of the farm or its subset or of the farm or field, and knowledge of the unique codes specific to said other animal farms or farm subsets, or said other farms or fields, to compute and propose to a farmer which isotope(s) and which amounts must be added or depleted in order to define the isotropic food and which diet with said isotropic food in order to deliver said food to said animals from the farm or farm subset so that said animals have the unique code specific to the moment of the slaughter, and to respectively feed the plants so that said plants also have the unique code specific to the moment of the harvest.

12. The method according to claim 5, wherein the unique code integrates:
- an isotopic signature of several rare elements, say at least 5 of the following elements: La, Ce, Pr, Nd, Pm, Sm, Eu, Dg, Tb, Dy, Ho, Er, Tm, Yb, Lu, these rare elements being associated with the geographical location of the farm or of the farm or field, at the continent, country or region level,
- an isotopic signature of at least 5 of the elements Li, Be, B, F, Na, Mg, Al, P, Cl, K, Ca, Ti, V, Cr, Mn, Fe, Co, Ni, Cu, Zn, Ga, Ge, As, Se, Rb, Sr, Y, Zr, Nb, Mo, Rh, Pd, Ag, Cd, Sn, Sb, Te, I, Ba, Hf, Ta, W, Re, Ir, Hg, Ti, Pb, Si, the latter being related to the identity of the animal farm or its subset, or the farm or field, and
- an isotropic signature of the elements C, O, N, H, S.

13. The method according to claim 5, wherein i further comprises measuring at least two chemical elements selected from the group consisting of C, H, O, N, and S or their isotopes in the food and/or water for each farming or growing cycle.

14. The method according to claim 13, wherein the unique code comprises natural ratios of elements or isotopes of elements from the farm or crop coming from the soil, water and food, and imposes concentrations or ratios of other elements or their isotopes, which imposed concentrations or ratios are the result of the elements or isotopes brought by the water and/or food over a sub-period of the farming or growing period.

15. The method according to claim 14, wherein the unique code comprises natural ratios of isotopes of at least 5 of the elements Sr, B, Li, Ca, Na, Mg, K, F, P, Cl, As, Pb, Cd and all of the elements C, H, O, N, S.

16. The method according to claim 14, wherein the unique code comprises imposed isotope concentrations or ratios for at least 3 elements selected from the group consisting of Be, Al, Ti, V, Cr, Mn, Fe, Co, Ni, Cu, Zn, Ga, Ge, Se, Rb, Y, Zr, Nb, Mo, Rh, Pd, Ag, Sn, Sb, Te, I, Ba, Hf, Ta, W, Re, Ir, Hg, Ti, and Si.

17. The method according to claim 5, wherein:
- the data measured under i. are entered in the computer or the database, which computer, through its programmable logic unit, determines the BGS, which establishes the reference starting base for a given site,
- the computer or the database also stores the unique codes specific to other farms or farm subsets, or other farms or fields, that have been established during an earlier period,
- the computer or the database stores the data of the accumulation rate of the animals of the farm or subset, or plants, and the computer has computing means establishing a correlation between a variation in abundance of isotope elements and the feeding diet with the isotopic food, in order to obtain a unique code of the time of slaughter, respectively harvest,
- the unique code and the isotopic food are determined by the computer in order that the code be unique and thus distinguishable from all the other unique codes determined for other farms or fields and stored in said computer or database.

18. The method according to claim 5, wherein the computer proposes a diet that enrich with one or several isotopes, or deplete with one or several isotopes, or combine enrichment and depletion, with respect to what an unmodified diet would contribute to the animals or plants during a given cycle.

19. The method according to claim 17, wherein the computer proposes a diet that enrich with one or several isotopes, or deplete with one or several isotopes, or combine enrichment and depletion, with respect to what an unmodified diet would contribute to the animals or plants during a given cycle.

20. The method according to claim 18, wherein an isotopic variation on 1, 2, 3 or more elements is applied.

* * * * *